United States Patent [19]

Ayers

[11] Patent Number: 5,395,373

[45] Date of Patent: Mar. 7, 1995

[54] ATRIAL DEFIBRILLATOR AND METHOD FOR SETTING ENERGY THRESHOLD VALUES

[75] Inventor: Gregory M. Ayers, Duvall, Wash.

[73] Assignee: InControl, Inc., Redmond, Wash.

[21] Appl. No.: 1,454

[22] Filed: Jan. 7, 1993

[51] Int. Cl.[6] .............................................. A61N 1/39
[52] U.S. Cl. .......................................... 607/8; 607/5; 607/7
[58] Field of Search ......................... 607/8, 7, 5, 4, 14

[56] References Cited

U.S. PATENT DOCUMENTS

| | | |
|---|---|---|
| 3,952,750 | 4/1976 | Mirowski et al. . |
| 4,316,472 | 2/1982 | Mirowski et al. . |
| 4,572,191 | 2/1986 | Mirowski et al. . |
| 5,105,809 | 4/1992 | Bach, Jr. et al. ..................... 607/5 |
| 5,129,392 | 7/1992 | Bardy et al. ........................ 607/27 |
| 5,165,403 | 11/1992 | Mehra . |
| 5,279,293 | 1/1994 | Andersen et al. .................... 607/5 |

OTHER PUBLICATIONS

Schwingshackl et al., "Digital System for Artificial Fibrillation of Animal Hearts", Biomedical Engr, Nov. 1973, vol. 8, No. 11, pp. 472–474.

Levy et al., "Cardiac Fib–Defib: Use of Elect. current in Conversion of Cardiac Rhythm," American J. of Med. Elect., Oct.–Dec. 1964, pp. 242–248.

Abstract:"Low Energy Pulsing on the T-Wave: A New Programming Method for Intentional, Device Mediated Induction of Ventricular Fibrillation for Defibrillation Testing", Bardy et al.

Presented at the 13th Annual Scientific Session of the North American Society of Pacing and Clinical Electrophysiology, May 14–16 1992, No. 217.

Article: "New Method for Terminating Cardiac Arrhythmias", Lown, et al., JAMA, vol. 182, No. 5, Nov. 3, 1962.

Primary Examiner—William E. Kamm
Assistant Examiner—Kennedy J. Schaetzle
Attorney, Agent, or Firm—Richard O. Gray, Jr.

[57] ABSTRACT

An implantable atrial defibrillator cardioverts the atria of a patient's heart and determines the quantity of cardioverting electrical energy required for cardioverting the atria of the patient. The atrial defibrillator includes a detector for detecting atrial activity of the heart and an atrial fibrillation detector for determining when the atria of the heart are in fibrillation. A delivery stage is selectively operable in a test mode for applying fibrillation inducing electrical energy to the atria when the atria are not in fibrillation for inducing fibrillation. When fibrillation is induced, the delivery stage repeatedly applies test cardioversion electrical energy to the atria until the atria are cardioverted. Thereafter, a value indicative of the quantity of the test cardioversion energy last applied to the atria is stored for future reference when the atrial defibrillator is in a normal operating mode.

14 Claims, 2 Drawing Sheets

ATRIAL DEFIBRILLATOR AND METHOD FOR SETTING ENERGY THRESHOLD VALUES

BACKGROUND OF THE INVENTION

The present invention generally relates to an atrial defibrillator for applying cardioverting electrical energy to the atria of a human heart in need of cardioversion. The present invention is more particularly directed to a fully automatic implantable atrial defibrillator which is selectively operable in a test mode for setting a threshold level for the cardioverting electrical energy. More specifically, the atrial defibrillator of the present invention, when the test mode is enabled by a physician, induces atrial fibrillation when the atria are not in fibrillation and thereafter repeatedly applies cardioverting electrical energy to the atria with incrementally increased quantities of electrical energy until the atria are successfully cardioverted. Thereafter, a value indicative of the last applied quantity of energy is stored in memory for reference during subsequent normal operation.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchrony with a detected electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has precluded these defibrillators from becoming a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

Improved atrial defibrillators and lead systems which exhibit both automatic operation and improved safety are fully described in copending U.S. applications, Ser. No. 07/685,130, filed Apr. 12, 1991, in the names of John M. Adams and Clifton A. Alferness for IMPROVED ATRIAL DEFIBRILLATOR AND METHOD and Ser, No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention and incorporated herein by reference. The atrial defibrillators disclosed in the referenced applications include an atrial fibrillation detector which automatically detects when the atria are in fibrillation and in need of cardioversion and a cardioverter stage which, responsive to the atrial fibrillation detector detecting atria fibrillation, automatically delivers cardioverting electrical energy to the atria.

Once an atrial defibrillator is implanted, it is desirable at periodic intervals to set the quantity of cardioverting electrical energy delivered to the atria at an energy level which provides a high probability of successful cardioversion but which is not excessively large. This is due to the fact that the electrical energy to cardiovert the atria may be painful to the patient or at least cause discomfort. Hence, it is most desirable to set the energy level to just above a threshold level which will provide the high probability of successful cardioversion. Since the threshold level will be different for each patient and changes over time, it is necessary for the physician to induce atrial fibrillation in a patient and then perform a series of cardioverting electrical energy applications to the atria at incrementally increasing energy levels until the threshold level is determined by the successful cardioversion of the atria. The series of applications is preferably started at a low energy believed to be insufficient to cardiovert the atria of the patient.

One method of inducing atrial fibrillation in a patient is to apply rapid pacing pulses to the atria or apply a series of premature pacing pulses to the atria of the patient. This approach however has severe ramifications.

Firstly, if the rapid pacing pulses are provided by the atrial defibrillator through the atrial defibrillator implanted lead system, the energy required to induce atrial fibrillation may cause excessive drain on the depletable power source, such as a battery, which supplies power to the implanted defibrillator. This excessive drain can prematurely deplete the atrial defibrillator battery and require more frequent replacement of the atrial defibrillator than desired. If the pacing pulses are not applied by the implanted defibrillator, but by an external pacing source, an additional catheter lead is required necessitating an invasive procedure to at least temporarily implant the additional catheter. This not only causes inconvenience and discomfort to the patient but additionally imposes mobility restraints of more than four hours on the patient and the concomitant mortality associated with such a procedure. Furthermore, with such rapid atrial pacing, there is always the probability of inducing undesirable other arrhythmias of the heart.

The atrial defibrillator of the present invention overcomes the disadvantages expressed above with respect to the above described method of inducing atrial fibrillation for the purpose of permitting the determination of a patient's atrial defibrillation energy threshold level. The atrial defibrillator of the present invention is selectively operable, by a physician, into a test mode wherein, in the absence of natural atrial fibrillation, electrical energy is applied to the atria having a quantity less than the quantity required for atrial defibrillation or cardioversion and at a time during the cardiac cycle of the heart when the heart is most vulnerable to the inducement of atrial fibrillation. More particularly, the electrical energy is applied in timed relation to a sensed electrical activation (R wave) of the heart and preferably in synchrony with a sensed R wave which, in most patients, occurs in time closely to the relative refractory of the atria. The atrial fibrillation inducing electrical energy is thus applied at a time during the cardiac cycle of the heart when the heart is most vulnerable to induced atrial fibrillation. In general, only one such application of electrical energy will be required for inducing atrial fibrillation. However, if more than one such application is required, the atrial defibrillator provides additional atrial fibrillation inducing electrical energy applications to the atria until atrial fibrillation is induced. Even if more than one such application is required, since the energy is applied when the heart is most vulnerable to induced atrial fibrillation, only a limited number of such applications will be required. This reduces the amount of total electrical energy required to induce atrial fibrillation as compared to the total energy required with rapid atrial pacing to accomplish this purpose. Hence, the atrial fibrillation is induced by the atrial defibrillator and its implanted lead system to thus negate the need for an invasive procedure for the temporary implantation of an additional catheter. Also, since the energy is applied in synchrony with an R wave, the inducement of ventricular fibrillation or other undesirable arrhythmias is avoided.

As will be seen hereinafter, and in accordance with the present invention, when atrial fibrillation is successfully induced, the atrial defibrillator, while still in the test mode, provides a series of cardioverting electrical energy applications to the atria. The cardioverting applications begin at an energy level which is lower than that expected for successful cardioversion and the energy level is incrementally increased for each application. When cardioversion of the atria is successful, a value corresponding to the last quantity of cardioverting electrical energy applied to the atria is stored in a memory for later reference in treating natural atrial fibrillation and the atrial defibrillator exits the test mode and reenters its normal mode of operation for cardioverting the atria when the atria are in need of cardioversion.

SUMMARY OF THE INVENTION

The invention therefore provides an implantable atrial defibrillator adapted to be implanted beneath the skin of a patient for cardioverting the atria of a patient's heart when the atria are in need of cardioversion. The atrial defibrillator includes first sensing means for sensing atrial activity of the heart and atrial fibrillation detecting means responsive to the first sensing means for determining when the atria of the heart are in fibrillation and in need of cardioversion and when the atria of the heart are not in fibrillation. The atrial defibrillator further includes applying means for applying electrical energy to the atria of the patient's heart wherein the applying means is selectively operable and responsive to the atrial fibrillation detecting means for applying first electrical energy to the atria for inducing fibrillation of the atria of the patient's heart when the atria of the heart are not in fibrillation and selectively operable and responsive to the atrial fibrillation detecting means for applying second electrical energy to the atria for cardioverting the atria of the patient's heart when the atria are in fibrillation and in need of cardioversion.

The present invention further provides an implantable atrial defibrillator adapted to be implanted beneath the skin of a patient for applying cardioverting electrical energy to the atria of a patient's heart when the atria are in fibrillation and in need of cardioversion and being selectively operable in a test mode for setting the quantity of the cardioverting electrical energy to a threshold quantity. The atrial defibrillator includes first sensing means for sensing atrial activity of the heart, atrial fibrillation detecting means responsive to the first sensing means for determining when the atria of the heart are in fibrillation and in need of cardioversion and when the atria of the heart are not in fibrillation and second sensing means for sensing electrical activations of the heart. The atrial defibrillator further includes enable means for selectively rendering the atrial defibrillator in the test mode and applying means responsive to the enable means, to the second sensing means, and to the atrial fibrillation detecting means determining that the atria are not in fibrillation for applying first electrical energy to the atria in timed relation to a sensed electrical activation of the heart to induce fibrillation of the atria. The applying means are further responsive to the atrial fibrillation detecting means determining that the atria are in fibrillation for repeatedly applying second electrical energy to the atria until the atrial fibrillation detecting means determines that the atria are not in fibrillation. The applying means increases the quantity of the second electrical energy with each repeated application. The atrial defibrillator further includes means for storing a value, indicative of the quantity of the second electrical energy last applied to the atria, as the threshold quantity.

The present invention still further provides a method for use in an implantable atrial defibrillator adapted to be implanted beneath the skin of a patient for applying cardioverting electrical energy to the atria of a patient's heart when the atria are in fibrillation and in need of cardioversion for setting the quantity of the cardioverting electrical energy to a threshold quantity. The method includes the steps of sensing atrial activity of the heart, determining responsive to the sensed atrial activity when the atria of the heart are in fibrillation, applying, responsive to determining that the atria are not in fibrillation, first electrical energy to the atria to induce fibrillation of the atria and determining that the atria are in fibrillation. The method includes the further steps of repeatedly applying second electrical energy to the atria until the atria are not in fibrillation wherein the quantity of the second electrical energy is increased with each repeated application and storing a value, indicative of the quantity of the second electrical energy last applied to the atria, as the threshold quantity.

The present invention still further provides an atrial defibrillator implantable beneath the skin of a patient wherein the atrial defibrillator is operative in a mode for inducing atrial fibrillation of a patient's heart. The atrial defibrillator includes discharge means for delivering electrical energy to the atria of the heart, sensing means for sensing electrical activations of the heart, and means for receiving an enable command from external to the skin of the patient. The discharge means are responsive to the enable command and the sensing means for delivering the electrical energy to the atria in synchrony with a sensed electrical activation of the heart.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
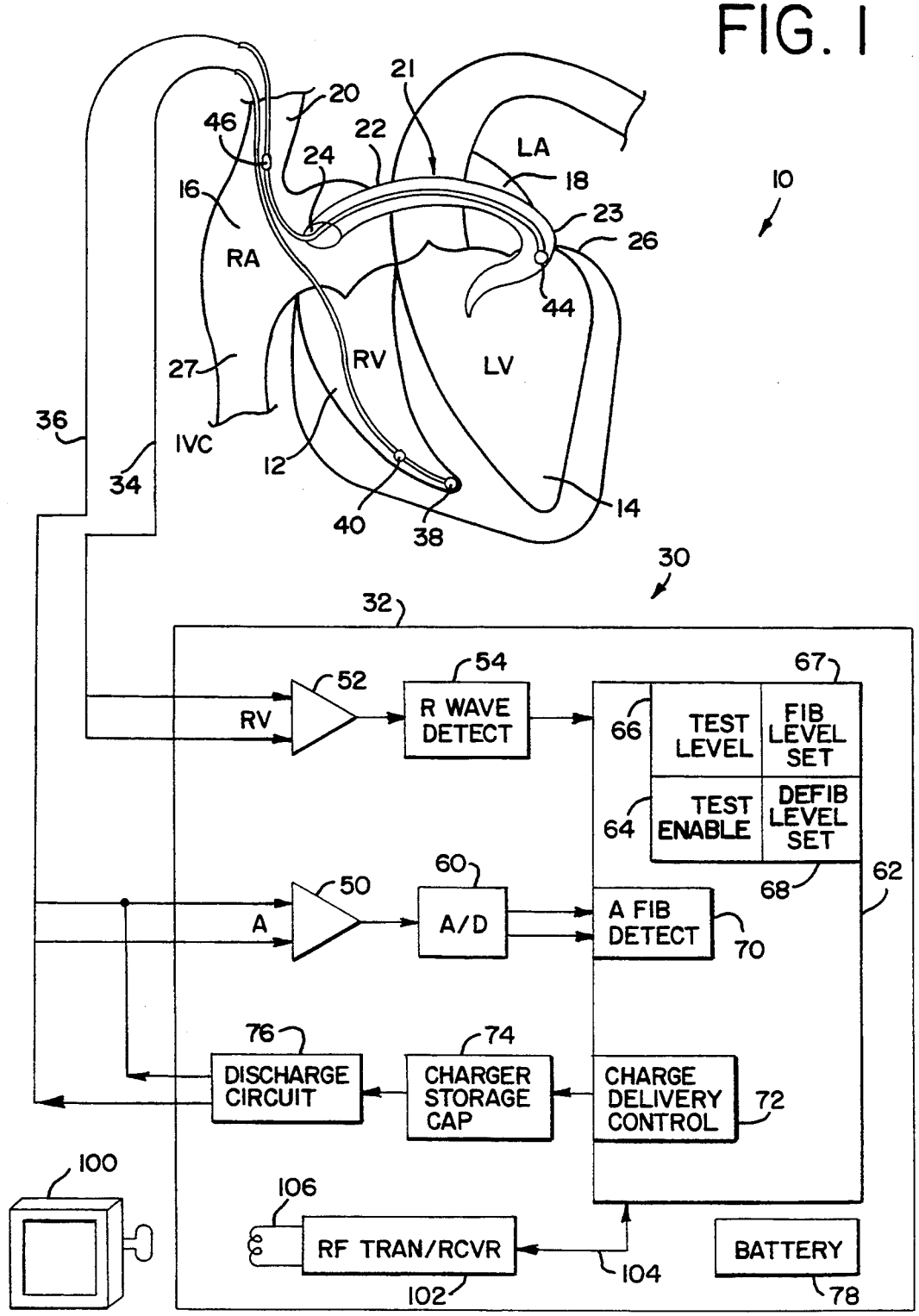
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "electrical activations" denotes R waves of the heart cardiac cycle which are depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial hi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is preferably fed through the superior vena cava 20, into the right atrium 16, and then into the right ventricle 12 as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart. The intravascular second lead 36, and more particularly the first electrode 44 and the second electrode 46 further provide for the delivery of atrial fibrillation inducing electrical energy to the atria in a manner to be described hereinafter.

Within the enclosure 32, the atrial defibrillator 30 includes a first sense amplifier 50, a second sense amplifier 52, and an R wave detector 54. The first sense amplifier 50 forms a first sensing means which, together with the first electrode 44 and second electrode 46 of the second lead 36 to which it is coupled detects atrial activity of the heart. The second sense amplifier 52 and the R wave detector 54 form a second sensing means which together with the first lead 34 to which sense amplifier 52 is coupled, senses ventricular activations of the right ventricle 12.

The output of the first sense amplifier 50 is coupled to an analog to digital converter 60 which converts the analog signal representative of the sensed atrial activity of the heart to digital samples for further processing in a manner to be described hereinafter. The output of the second sense amplifier 52 is coupled to the R wave detector 54. The R wave detector 54 is of the type well known in the art which provides an output pulse upon the occurrence of an R wave being sensed during a cardiac cycle of the heart.

The enclosure 32 of the atrial defibrillator 30 further includes a microprocessor 62. The microprocessor 62 is preferably implemented in a manner as disclosed in the aforementioned copending U.S. applications, Ser. Nos. 07/685,130 and 07/856,514 and further as described hereinafter with respect to the flow diagram of FIG. 2. The implementation of the microprocessor 62 in accordance with this embodiment of the present invention results in a plurality of functional stages. The stages include a test enable 64, a test level set stage 66, a fibrillation level set stage 67, a defibrillation level set or storage stage 68, an atrial arrhythmia detector in the form of an atrial fibrillation detector 70, and a charge delivery and energy control stage 72.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and coveys the data to the memory 92 over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, such as fibrillation energy levels into stage 67 or defibrillation energy levels into stage 68, or for receiving operating commands such as a test enable command, the microprocessor 62 receives the programmable operating parameters and operating commands from an external controller 100 which is external to the skin of the patient and under the control of an operator, such as a physician. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters and operating commands from the external controller 100 which the receiver/transmitter 102 then conveys to the microprocessor 62 for storage in interval memory, such as stages 67 and 68, or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a charger and storage capacitor circuit 74 of the type well known in the art which charges a storage capacitor to a predetermined voltage level and a discharge circuit 76 for discharging the storage capacitor within circuit 74 by a predetermined amount to provide a controlled discharge output of electrical energy when required to the atria of the heart. To that end, the discharge circuit 76 is coupled to the first electrode 44 and the second electrode 46 of the second lead 36 for applying the cardioverting or defibrillating electrical energy to the atria and for applying atrial fibrillation inducing electrical energy to the atria. Lastly, the defibrillator 30 includes a depletable power source 78, such a lithium battery, for providing power to the electrical components of the atrial defibrillator 30.

When the atrial defibrillator 30 is operative in its normal operating mode, the sense amplifier 52 and the R wave detector 54 continuously detect the occurrence of electrical activations of the right ventricle 12. As disclosed in the aforementioned copending U.S. applications Ser. Nos. 07/685,130 and 07/856,514, herein incorporated by reference, when the time intervals between immediately successive R waves indicate the probability of an episode of atrial fibrillation, the microprocessor 62 enables the atrial fibrillation detector 70, sense amplifier 50, and the analog to digital converter 60. If the atrial fibrillation detector 70 determines that the atria 16 and 18 are in fibrillation and thus in need of cardioversion, the charge delivery control 72 causes the charger and storage capacitor circuit 74 to charge the storage capacitor within circuit 74 to a level set in the defibrillator level set stage 68. Then, when an electrical activation (R wave) is sensed by sense amplifier 52 and R wave detector 54, the charge delivery control 72 cause the discharge circuit 76 to discharge the capacitor in the charge storage circuit 74 into electrodes 44 and 46 for cardioverting the atria. The foregoing is repeated until the atria are successfully cardioverted.

In accordance with the present invention, the atrial defibrillator 30 is also selectively operable in a test mode for determining the defibrillation energy threshold level of the patient for providing the defibrillation level set stage 68 with a value for reference by the atrial defibrillator in its normal operation so that the defibrillating electrical energy applied to the atria is of a quantity which provides a high probability of successful cardioversion but which is not excessively large. The implementation of the atrial defibrillator 30 to that end is illustrated in FIG. 2.

Figure 2:
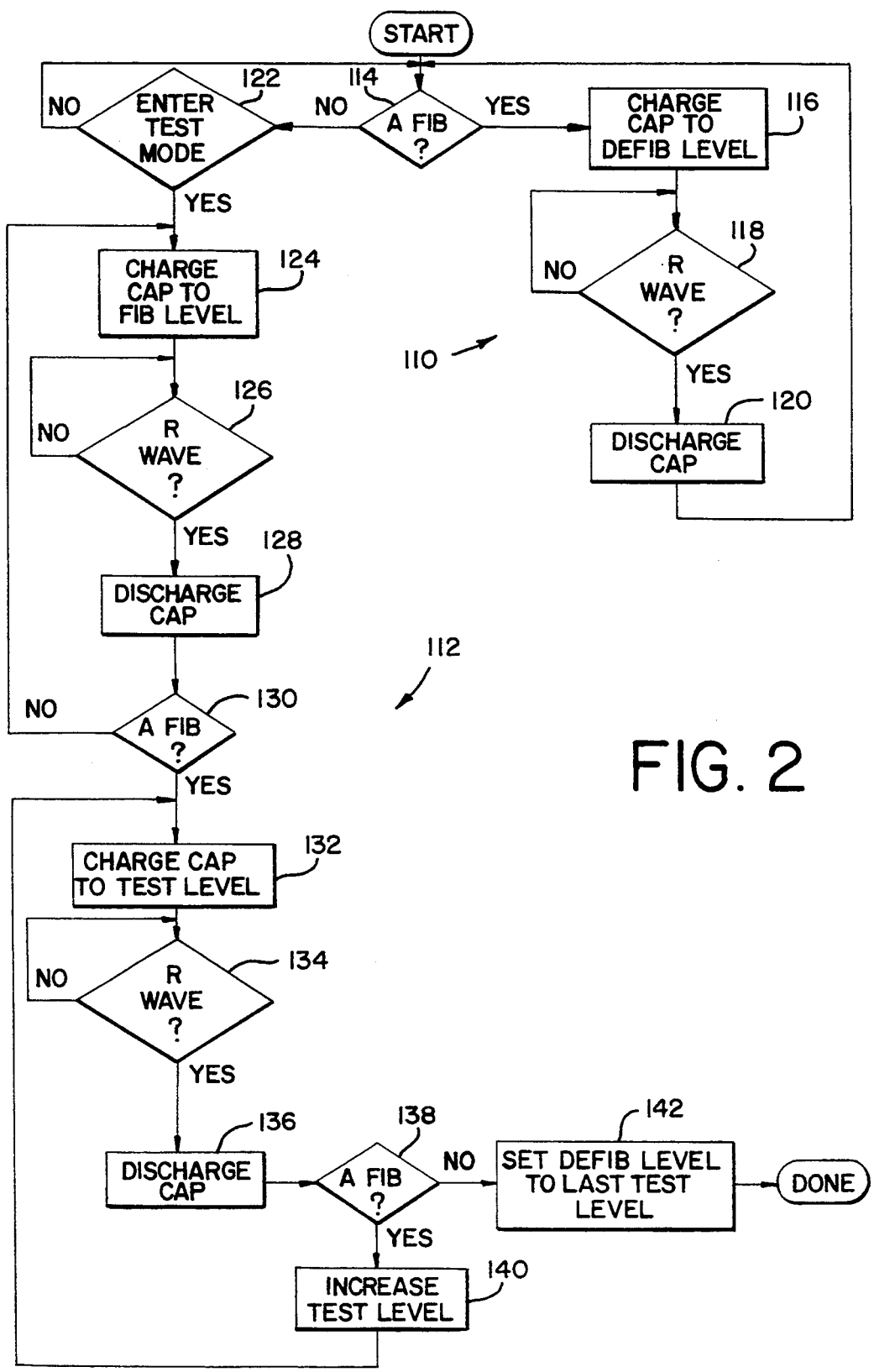
FIG. 2 is a flow diagram illustrating the manner in which the atrial defibrillator of FIG. 1 may be implemented in accordance with the present invention for inducing atrial fibrillation of the heart and thereafter applying defibrillating or cardioverting electrical energy to the atria of the heart to determine the atrial cardioversion threshold level of the heart.

Referring now to FIG. 2, it illustrates, in flow diagram format, the implementation of the atrial defibrillator 30 for both the normal operating mode and the test operating mode. The normal operating mode is implemented in accordance with a normal operating mode section 110 and the test mode is implemented in accordance with a test mode section 112.

Both the normal operating mode and the test operating mode require interrogation of the atrial fibrillation detector 70 in accordance with step 114. If atrial fibrillation is detected in step 114, the capacitor within the charger storage circuit 74 is charged in step 116 to the level set in the defibrillation level set stage 68. Thereafter, in step 118, it is determined if an electrical activation (R wave) is detected by sense amplifier 52 and R wave detector 54. When an R wave is detected in step 118, the microprocessor then causes the discharge circuit 76 to discharge the storage capacitor of circuit 74 in accordance with step 120. The energy discharge from the storage capacitor is delivered to the electrodes 44 and 46 for application across the atria 16 and 18 for cardioverting the atria. After the capacitor has been discharged, the microprocessor returns to once again interrogate the atrial fibrillation detector. Upon repeating step 114, if atrial fibrillation is still present, steps 116, 118, and 120 are then repeated. If the atria are successfully cardioverted, the atrial defibrillator 30 returns to normal sensing.

When it is desired to enter the test mode, the physician transmits from the external controller 100 a test enable command to the transmitter/receiver 102 of the atrial defibrillator 30. The test enable command is conveyed to the test enable stage 64 of microprocessor 62 to set the test enable stage 64.

If it is determined in step 114 that the atria are not in fibrillation, the microprocessor then determines in step 122 if the test enable stage 64 has been set. If the test enable stage has not been set, the microprocessor returns to start. If the test enable stage has been set, the charge delivery control 72 then causes the capacitor within the charger storage circuit 74 to be charged to a level previously entered into the fibrillation level set stage 67. The capacitor is thus charged in accordance with step 124. The fibrillation level is preferably a quantity of energy which is less than the quantity of energy for defibrillating the atria. For example, the electrical energy for defibrillating the energy may be in a range of 0.5 to 3.0 joules and preferably between 0.5 and 1 joule. In contrast, the quantity of energy for inducing fibrillation may be in a range of 0.05 to 0.4 joules and preferably 0.1 joule.

Following step 124, the atrial defibrillator 30 determines in step 126 if an R wave has been detected. When an R wave is detected in step 126, the atrial defibrillator immediately thereafter in step 128 discharges the capacitor of the charger storage circuit 74 across the atria by applying the discharged energy to electrodes 44 and 46 of the second lead 36. As previously mentioned, the fibrillation inducing energy is preferably applied to the atria in synchronism with an R wave because, in most patients, a sensed R wave will occur in time in substantial correspondence to the T wave of the atria and hence, at a time when the atria are most vulnerable to induced fibrillation. Once the fibrillation inducing electrical energy is applied to the atria, the atrial fibrillation detector 70 is once again interrogated in step 130. If the atria are not in fibrillation, the atrial defibrillator then returns to repeat steps 124, 126, 128, and 130. As previously mentioned, in most cases, a single application of fibrillation inducing electrical energy will only be required to induce atrial fibrillation.

Once atrial fibrillation is induced, the atrial defibrillator then proceeds to step 132 for charging the capacitor in the charger storage circuit 74 to an initial test level in accordance with an initial test level value provided by the test level stage 66. The initial test level is preferably a level which is not expected to provide successful cardioversion of the atria. This assures that the determination of the patient's threshold level begins at a level below the expected threshold level.

Following step 132, the atrial defibrillator then in step 134 determines when an R wave is sensed by sense amplifier 52 and R wave detector 54. When an R wave is sensed, the capacitor in circuit 74 is discharged by the discharge circuit 76 in step 136.

Following step 136, the atrial fibrillation detector 70 is interrogated in step 138 to determine if the application of the test cardioversion energy is successful in cardioverting the atria. If the atrial fibrillation detector 70 indicates that the atria are still in fibrillation, the defibrillator then in step 140 incrementally increases the test level by, for example, 0.2 joules, and returns to step 132 for repeating step 132, 134, 136, and 138. This results in repeated applications of cardioverting electrical energy to the atria with each application being incrementally increased over the immediately preceding application.

When it is determined in step 138 that the atria have been successfully cardioverted, the atrial defibrillator then in step 142 enters into the defibrillation level set stage 68 a value corresponding to the last test level utilized which was successful in cardioverting the atria. Also in step 142, the test enable stage 64 may be reset for exiting the test mode at which point the atrial defibrillator reenters the normal operating mode. The defibrillation level set stage 68 will then contain a value corresponding to the last test level utilized during the test mode and hence the proper threshold level for the individual patient.

While a particular embodiment of the present invention has been shown and described, modifications may be made, and it is therefore intended in the appended claims to cover all such changes and modifications which fall within the true spirit and scope of the invention.

What is claimed is:

1. An implantable atrial defibrillator adapted to be implanted beneath the skin of a patient for cardioverting the atria of a patient's heart when the atria are in need of cardioversion, said atrial defibrillator comprising:

first sensing means for sensing atrial activity of the heart;

atrial fibrillation detecting means responsive to said first sensing means for determining when the atria of the heart are in fibrillation and in need of cardioversion and when the atria of the heart are not in fibrillation; and applying means for applying electrical energy to the atria of the patient's heart during a predetermined portion of a cardiac cycle of the heart, said applying means being responsive to said atrial fibrillation detecting means for applying first electrical energy to the atria for inducing fibrillation of the atria of the patient's heart when the atria of the heart are not in fibrillation and responsive to said atrial fibrillation detecting means for applying second electrical energy to the atria for cardioverting the atria of the patient's heart when the atria are in fibrillation and in need of cardioversion, wherein said first electrical energy is of lesser quantity than said second electrical energy.

2. An atrial defibrillator as defined in claim 1 further including second sensing means for sensing electrical activations of the heart and wherein said applying means is responsive to said second sensing means for applying said first electrical energy during an electrical activation of the heart.

3. An atrial defibrillator as defined in claim 1 wherein said applying means applies said second electrical energy having an initial quantity of energy and thereafter repeatedly applies said second electrical energy having incrementally increased quantities of energy until the atria are cardioverted.

4. An atrial defibrillator as defined in claim 3 wherein said atrial fibrillation detecting means determines if the atria are in fibrillation after each repeated application of said second electrical energy and wherein said applying means is responsive to said atrial fibrillation detecting means for terminating said repeated application of said second electrical energy.

5. An atrial defibrillator as defined in claim 4 further including storing means for storing a value indicative of the last quantity of said second electrical energy applied to the atria of the heart.

6. An atrial defibrillator as defined in claim 1 further including enable means for selectively enabling said applying means to apply said first electrical energy to the atria.

7. An atrial defibrillator as defined in claim 1 wherein said applying means includes lead means for applying said first and second electrical energies to the atria of the heart.

8. An implantable atrial defibrillator adapted to be implanted beneath the skin of a patient for applying cardioverting electrical energy to the atria of a patient's heart when the atria are in fibrillation and in need of cardioversion, said atrial defibrillator being selectively operable in a test mode for setting the quantity of the cardioverting electrical energy to a threshold quantity and comprising:

first sensing means for sensing atrial activity of the heart;

atrial fibrillation detecting means responsive to said first sensing means for determining when the atria of the heart are in fibrillation and in need of cardioversion and when the atria of the heart are not in fibrillation;

second sensing means for sensing electrical activations of the heart;

enable means for selectively rendering said atrial defibrillator in said test mode;

applying means responsive to said enable means, to said second sensing means, and to said atrial fibrillation detecting means determining that the atria are not in fibrillation for applying first electrical energy to the atria in timed relation to a sensed electrical activation of the heart to induce fibrillation of the atria and responsive to said atrial fibrillation detecting means determining that the atria are in fibrillation for repeatedly applying second electrical energy to the atria until said atrial fibrillation detecting means determines that the atria are not in fibrillation, said applying means increasing the quantity of said second electrical energy with each said repeated application; and means for storing a value, indicative of the quantity of said second electrical energy last applied to the atria, as said threshold quantity.

9. An implantable atrial defibrillator adapted to be implanted beneath the skin of a patient for applying cardioverting electrical energy to the atria of a patient's heart when the atria are in fibrillation and in need of cardioversion, a method for setting the quantity of the cardioverting electrical energy to a threshold quantity and comprising the steps of:

sensing atrial activity of the heart;

determining responsive to the sensed atrial activity when the atria of the heart are not in fibrillation;

applying, responsive to determining that the atria are not in fibrillation, first electrical energy to the atria during a predetermined portion of a cardiac cycle of the heart to induce fibrillation of the atria;

determining that the atria are in fibrillation;

repeatedly applying second electrical energy to the atria until the atria are not in fibrillation, said last recited applying step including increasing the quantity of said second electrical energy with each said repeated application; and storing a value, indicative of the quantity of said second electrical energy last applied to the atria, as said threshold quantity.

10. A method as defined in claim 9 further including the step of sensing electrical activations of the heart and wherein said first recited applying step includes applying said first electrical energy during an electrical activation of the heart.

11. A method as defined in claim 9 wherein said first electrical energy is of lesser quantity than said second electrical energy.

12. A method as defined in claim 9 further including the steps of determining if the atria are in fibrillation after each repeated application of said second electrical energy.

13. A method as defined in claim 9 further including the step of providing lead means in electrical contact with the atria and wherein said applying steps include delivering said first and second electrical energies to said lead means.

14. In an atrial defibrillator implantable beneath the skin of a patient for cardioverting the atria of a patient's heart when the atria are in need of cardioversion, a means for inducing atrial fibrillation comprising:

sensing means for sensing ventricular electrical activations of the heart; and applying means for applying electrical energy to the atria for inducing fibrillation of the atria of the patient's heart, said applying means being responsive to said sensing means for applying said electrical energy to the atria in timed relation to a ventricular electrical activation of the patient's heart, and said electrical energy being of a quantity less than that required to cardiovert the atria.

* * * * *